United States Patent
Jang et al.

(10) Patent No.: US 7,961,109 B2
(45) Date of Patent: Jun. 14, 2011

(54) FALL DETECTING APPARATUS AND METHOD, AND EMERGENCY AID SYSTEM AND METHOD USING THE SAME

(75) Inventors: Jae-Won Jang, Daejon (KR);
Sa-Kwang Song, Daejon (KR);
Myung-Eun Lim, Daejon (KR);
Soo-Jun Park, Seoul (KR); Seon-Hee Park, Daejon (KR); Taehyoung Zyung, Daejon (KR); Soo-Young Oh, Daejon (KR)

(73) Assignee: Electronics and Telecommunications Research Institute, Daejon (KR)

( * ) Notice: Subject to any disclaimer, the term of this patent is extended or adjusted under 35 U.S.C. 154(b) by 495 days.

(21) Appl. No.: 11/950,302

(22) Filed: Dec. 4, 2007

(65) Prior Publication Data
US 2008/0133277 A1    Jun. 5, 2008

(30) Foreign Application Priority Data

Dec. 4, 2006  (KR) .................. 10-2006-0121221
Dec. 5, 2006  (KR) .................. 10-2006-0122511
Aug. 27, 2007 (KR) .................. 10-2007-0086074

(51) Int. Cl.
*G08B 23/00* (2006.01)
(52) U.S. Cl. ............. 340/573.1; 340/539.1; 340/539.17; 340/669; 340/689; 702/141
(58) Field of Classification Search ............... 340/573.1, 340/539.1, 573.7, 669, 689, 690; 702/141
See application file for complete search history.

(56) References Cited

U.S. PATENT DOCUMENTS

| | | | | |
|---|---|---|---|---|
| 6,433,690 B2 * | 8/2002 | Petelenz et al. | ............. | 340/573.1 |
| 7,028,547 B2 * | 4/2006 | Shiratori et al. | ................ | 73/495 |
| 7,299,159 B2 * | 11/2007 | Nanikashvili | ................ | 702/188 |
| 7,395,709 B2 * | 7/2008 | Noda et al. | ...................... | 73/510 |

(Continued)

FOREIGN PATENT DOCUMENTS

JP    2005-091219 A    4/2005

(Continued)

OTHER PUBLICATIONS

Tong Zhang et al, "Fall Detection by Embedding an Accelerometer in Cellphone and Using KFD Algorithm" International Journal of Computer Science and Network Security, vol. 6 No. 10 pp. 277-284, Oct. 2006.

(Continued)

*Primary Examiner* — Davetta W Goins
(74) *Attorney, Agent, or Firm* — Rabin & Berdo, P.C.

(57) ABSTRACT

Provided are a fall detecting apparatus and method and an emergency aid system and method using the same. The fall detecting apparatus includes a storing unit configured to store fall data vectors; an angular velocity measuring unit configured to measure an angular velocity value; an acceleration measuring unit configured to measure an acceleration value; an acceleration extracting unit configured to extract a kinetic acceleration value and a gravitational acceleration value by filtering the acceleration value measured by the acceleration measuring unit; and a fall determining unit configured to convert the angular velocity value, which is measured by the angular velocity measuring unit, and the kinetic acceleration value and the gravitational acceleration value, which are extracted by the acceleration extracting unit, into a fall data vector, and determine a use's fall by comparing the converted fall data vector with the fall data vector stored in the storing unit.

10 Claims, 7 Drawing Sheets

U.S. PATENT DOCUMENTS

| | | | |
|---|---|---|---|
| 7,423,537 B2 * | 9/2008 | Bonnet et al. | 340/573.1 |
| 2005/0232467 A1 * | 10/2005 | Mohri et al. | 382/103 |
| 2007/0073514 A1 * | 3/2007 | Nogimori et al. | 702/160 |

FOREIGN PATENT DOCUMENTS

| | | |
|---|---|---|
| KR | 2006-0111368 A | 10/2006 |
| WO | WO-2005/106503 | 11/2005 |

OTHER PUBLICATIONS

Jiann-I Pan et al., "An Intelligent Homecare Emergency Service System for Elder Falling", World Congress on Medical Physics and Biomedical Engineering, 2006, IFMBE Proceedings 14/1, p. 424.

Yue She et al., "An Interactive Editing Tool from Arbitrary Slices in 3D Ultrasound vol. Data", World Congress on Medical Physics and Biomedical Engineering, 2006, IFMBE Proceedings 14/4, p. 2447.

* cited by examiner

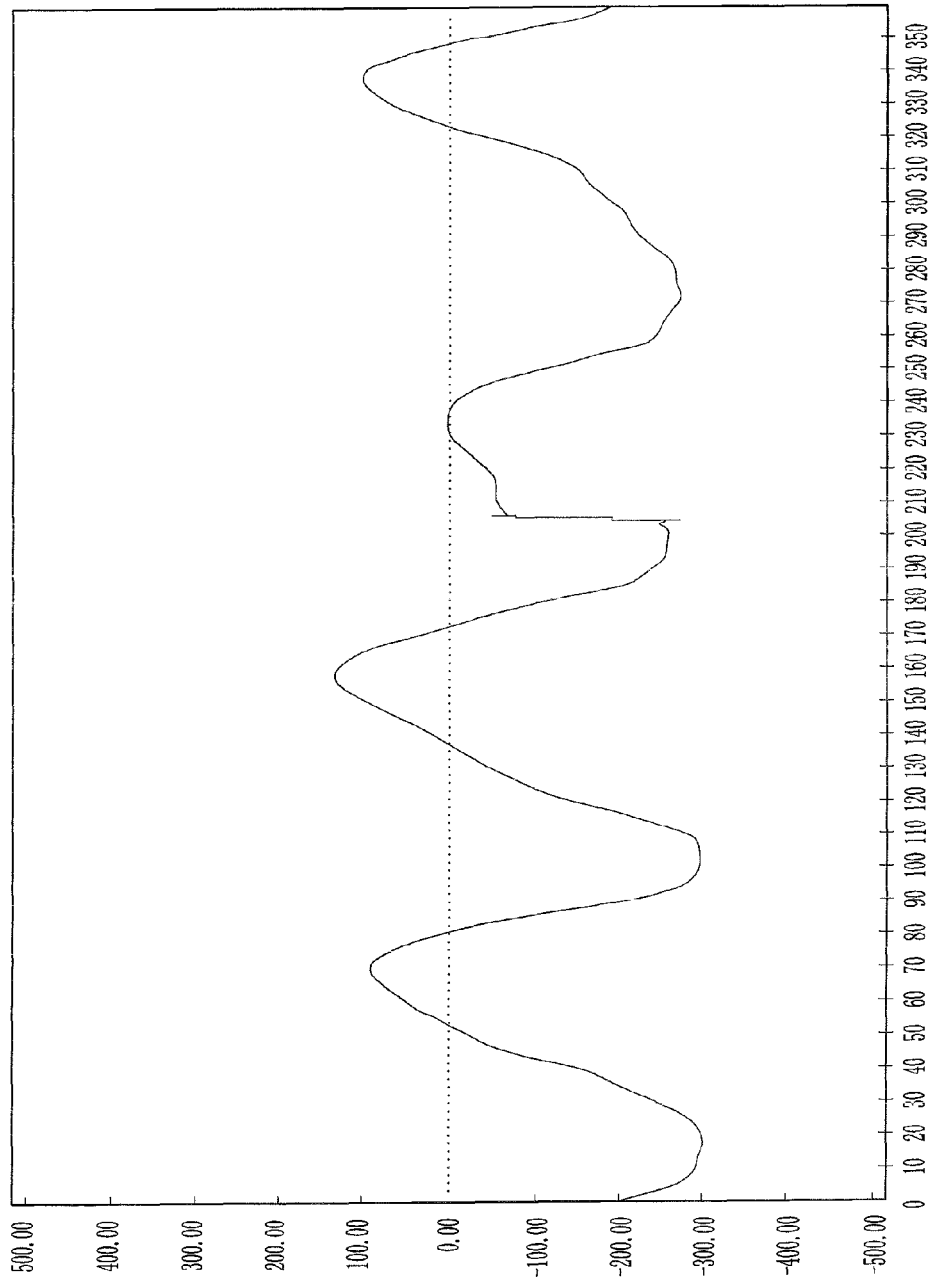

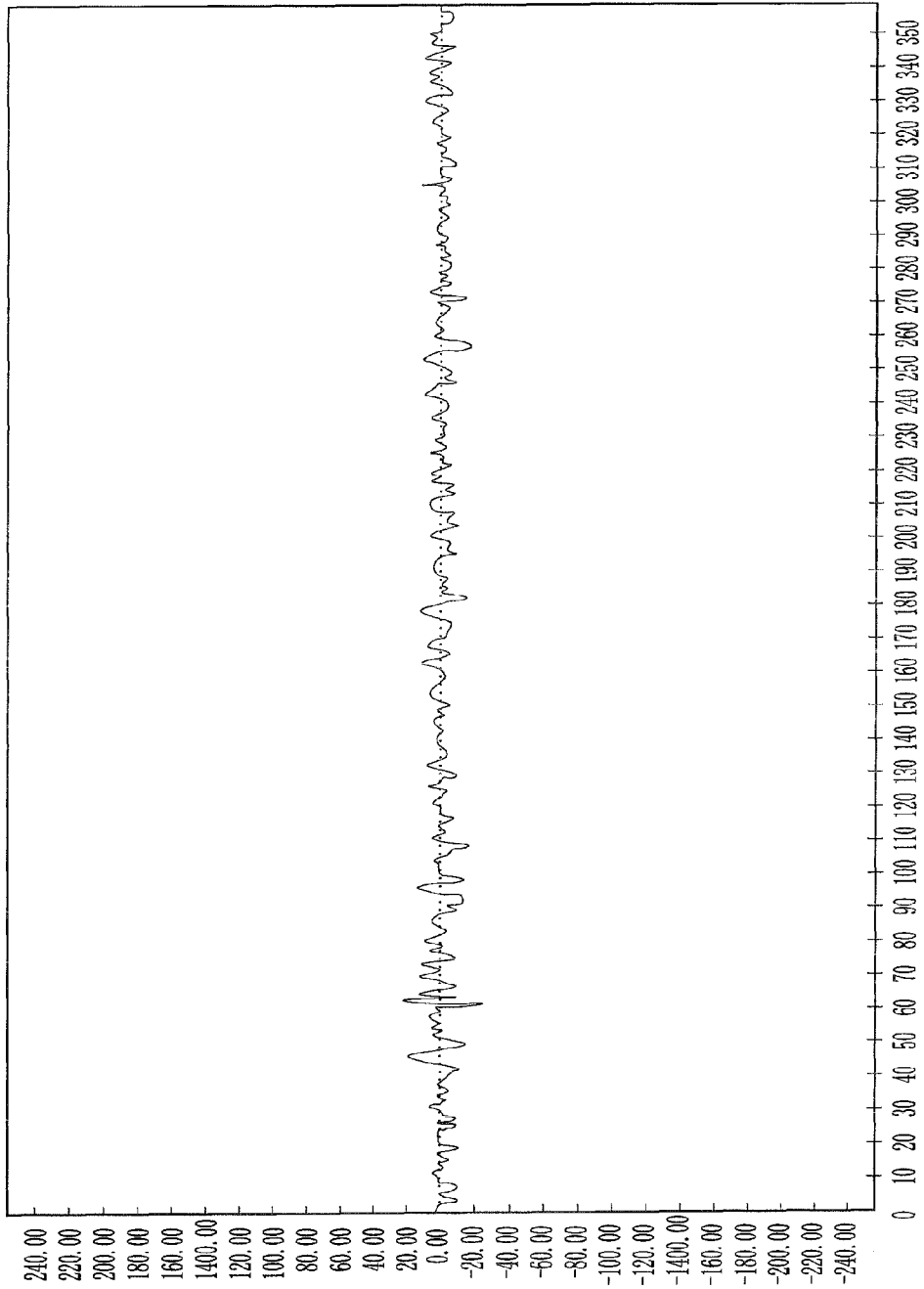

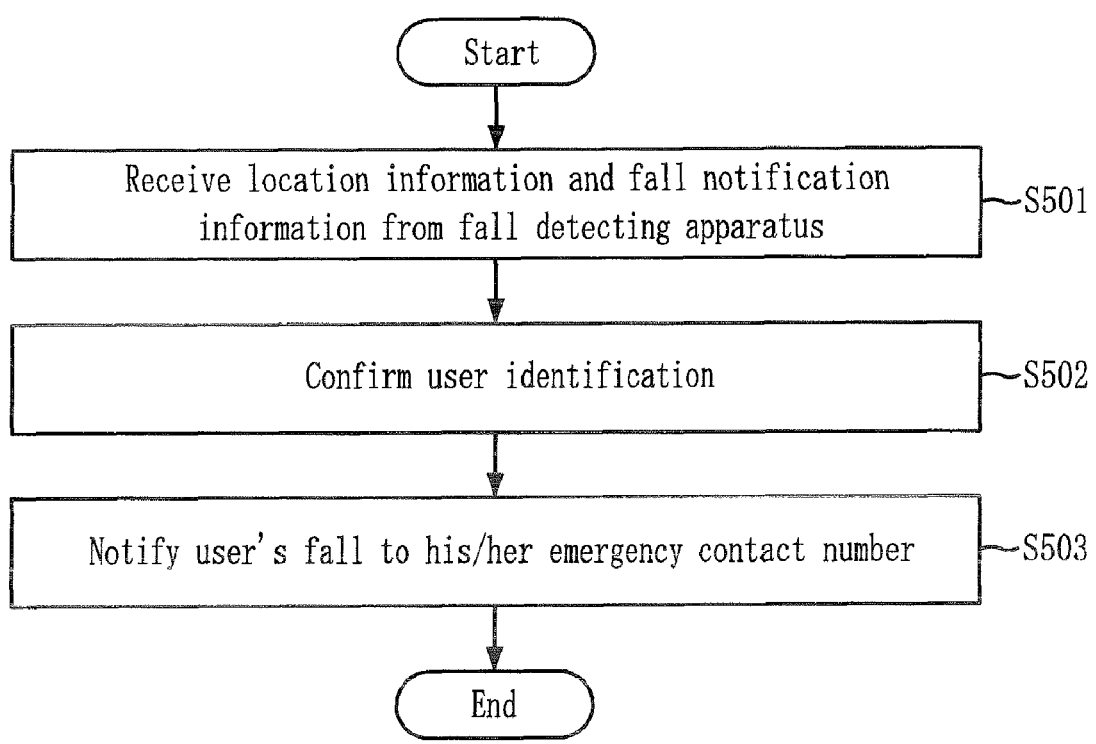

FALL DETECTING APPARATUS AND METHOD, AND EMERGENCY AID SYSTEM AND METHOD USING THE SAME

CROSS-REFERENCE(S) TO RELATED APPLICATIONS

The present invention claims priority of Korean Patent Application Nos. 10-2006-0121221, 10-2006-0122511, and 10-2007-0086074, filed on Dec. 4, 2006, Dec. 5, 2006 and Aug. 27, 2007, respectively, which are incorporated herein by reference.

BACKGROUND OF THE INVENTION

1. Field of the Invention

The present invention relates to a fall detecting apparatus and method and an emergency aid system and method using the same; and, more particularly, to a fall detecting apparatus and method and an emergency aid system and method using the same, which can quickly prevent a secondary accident caused by a fall by detecting, in real time, an accidental fall often occurring in everyday life of elderly persons or mobility-impaired persons and notifying the accidental fall to the emergency aid system.

This work was supported by the IT R&D program for MIC/IITA [2006-S-007-01, "Ubiquitous Health Monitoring Module and System Development"].

2. Description of Related Art

As the aging society has rapidly grown in recent years, a variety of healthcare services have been proposed which can help elderly persons or mobility-impaired persons enjoy a safe life everyday.

Especially, emergency aid systems for preventing unexpected accidents of solitary elderly persons who spend most of time alone have been introduced.

A conventional fall detecting method detects an occurrence of a fall when a triaxial acceleration measured using only a triaxial acceleration sensor exceeds a threshold value.

SUMMARY OF THE INVENTION

An embodiment of the present invention is directed to providing a fall detecting apparatus and method, which can solve a problem that has not correctly detected a fall because only a triaxial acceleration sensor is used.

Another embodiment of the present invention is directed to providing a fall detecting apparatus and method, which detects an accidental fall of an elderly person or mobility-impaired person in real time using data measured by an acceleration sensor and an angular velocity sensor, thereby providing a more correct fall detection.

Another embodiment of the present invention is directed to providing an emergency aid system and method, which can prevent a secondary injury of elderly persons or mobility-impaired persons due to their fall by notifying their guardians of the fall detected by the fall detecting apparatus.

Other objects and advantages of the present invention can be understood by the following description, and become apparent with reference to the embodiments of the present invention. Also, it is obvious to those skilled in the art to which the present invention pertains that the objects and advantages of the present invention can be realized by the means as claimed and combinations thereof.

In accordance with an aspect of the present invention, there is provided a fall detecting apparatus, including: a storing unit configured to store fall data vectors; an angular velocity measuring unit configured to measure an angular velocity value; an acceleration measuring unit configured to measure an acceleration value; an acceleration extracting unit configured to extract a kinetic acceleration value and a gravitational acceleration value by filtering the acceleration value measured by the acceleration measuring unit; and a fall determining unit configured to convert the angular velocity value, which is measured by the angular velocity measuring unit, and the kinetic acceleration value and the gravitational acceleration value, which are extracted by the acceleration extracting unit, into a fall data vector, and determine a use's fall by comparing the converted fall data vector with the fall data vector stored in the storing unit.

In accordance with another aspect of the present invention, there is provided a fall detecting method, including the steps of: measuring an angular velocity value and an acceleration value; extracting a kinetic acceleration value and a gravitational acceleration value by filtering the acceleration value; converting the measured angular velocity value, the measured kinetic acceleration value, and the measured gravitational acceleration value into a fall data vector; and determining a use's fall by comparing the converted fall data vector with a preset fall data vector.

In accordance with another aspect of the present invention, there is provided an emergency aid system, including: a user information storing unit configured to store personal information and health condition based on user's private number, and emergency contact number; a fall information receiving unit configured to receive location information and fall notification information from a fall detecting apparatus, which converts an angular velocity value, a kinetic acceleration value, and a gravitational value into a fall data vector and determines a user's fall by comparing the compared fall data vector with a preset fall data vector; a user identifying unit configured to confirm the user's identification by searching the user information storing unit on the basis of user's private number included in the fall notification information received by the fall information receiving unit; and a fall notifying unit configured to notify the user's fall to an emergency contact number of the user identified by the user identifying unit.

In accordance with another aspect of the present invention, there is provided an emergency aid method, including the steps of: receiving location information and fall notification information from a fall detecting apparatus, which converts an angular velocity value, a kinetic acceleration value, and a gravitational value into a fall data vector and determines a user's fall by comparing the compared fall data vector with a preset fall data vector; confirming the user's identification by searching a user information database on the basis of user's private number included in the received fall notification information; and notifying the user's fall to an emergency contact number of the identified user.

The present invention is formed in ultra-small size so that the elderly persons can easily wear the fall detecting apparatus in order to detect an accidental fall while monitoring walking and behavior patterns without interrupting elderly persons or mobility-impaired persons inside and outside a room. Accordingly, the present invention collects information on acceleration, angular velocity and slope in real time.

BRIEF DESCRIPTION OF THE DRAWINGS

FIG. 2B is a graph showing a gravitational acceleration value extracted by an acceleration extractor in accordance with an embodiment of the present invention.

FIG. 2C is a graph showing a kinetic acceleration value extracted by the acceleration extractor in accordance with an embodiment of the present invention.

FIG. 5 is a flowchart describing an emergency aid method using the fall detecting apparatus in accordance with an embodiment of the present invention.

DESCRIPTION OF SPECIFIC EMBODIMENTS

The advantages, features and aspects of the invention will become apparent from the following description of the embodiments with reference to the accompanying drawings, which is set forth hereinafter. Therefore, those skilled in the field of this art of the present invention can embody the technological concept and scope of the invention easily. In addition, if it is considered that detailed description on a related art may obscure the points of the present invention, the detailed description will not be provided herein. The preferred embodiments of the present invention will be described in detail hereinafter with reference to the attached drawings.

Figure 1:
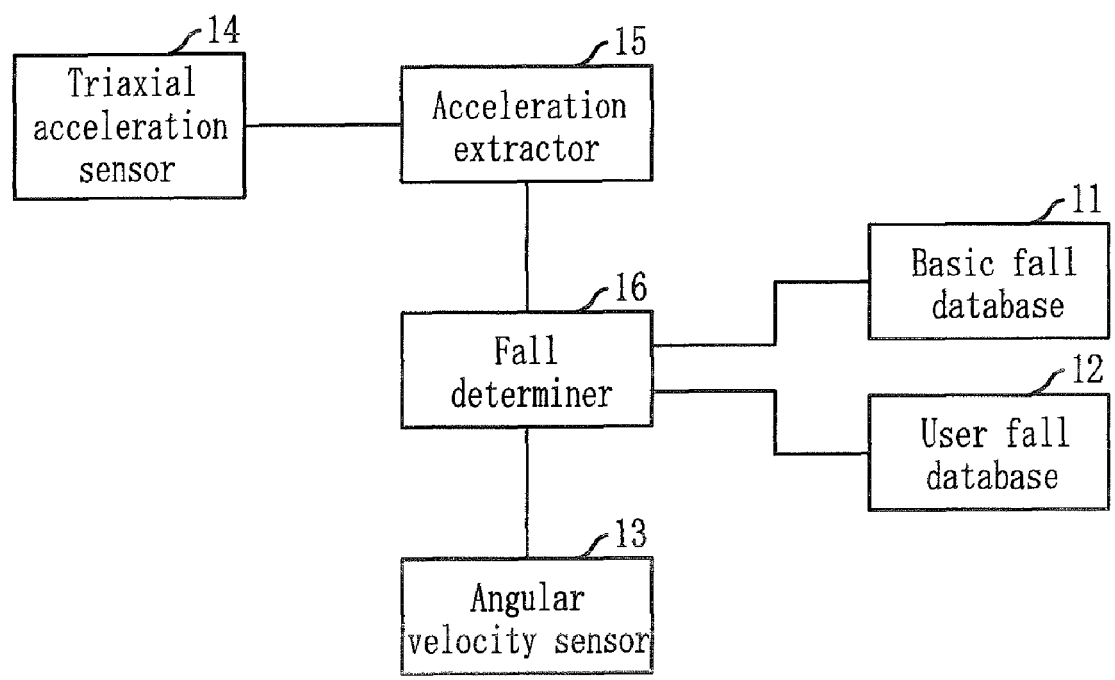
FIG. 1 is a block diagram of a fall detecting apparatus in accordance with an embodiment of the present invention.

FIG. 1 is a block diagram of a fall detecting apparatus in accordance with an embodiment of the present invention.

Referring to FIG. 1, the fall detecting apparatus includes a basic fall database 11 storing basic fall data vectors, a user fall database 12 storing user fall data vectors, an angular velocity sensor 13 periodically measuring an angular velocity value, a triaxial acceleration sensor 14 periodically measuring an acceleration value, an acceleration extractor 15 filtering the acceleration value measured by the triaxial acceleration sensor 14 to extract a kinetic acceleration value and a gravitational acceleration or slope value, and a fall determiner converting the angular velocity value, which is measured by the angular velocity sensor 13, and the kinetic acceleration value and the gravitational acceleration value, which are extracted by the acceleration extractor 15, into nine-dimensional fall data vector, and determining whether a user falls down or not by comparing the nine-dimensional fall data vector with the fall data vectors stored in the basic fall database 11 and the user fall database 12.

As one example, the fall determiner 16 stores the angular velocity value, which is measured by the angular velocity sensor 13, and the kinetic acceleration value and the gravitational acceleration value, which are extracted by the acceleration extractor 15, into a queue in form of nine-dimensional fall data vector, and determines whether the user falls down or not by comparing the fall data vector stored in the queue with the fall data vectors stored in the basic fall database 11 and the user fall database 12.

The fall detecting apparatus may further include a location information acquiring unit acquiring location information from a global positioning system (GPS) satellite, and a communication unit notifying the location information and fall notification information to an external emergency aid system when the fall determiner 16 determines that the user falls down. The fall notification information includes a user's private number. The location information acquiring unit may acquire the location information by using known location information acquiring techniques, instead of the GPS satellite.

The basic fall database 11 stores fall data vectors of general users, not dependent on the corresponding users, while the user fall database 12 stores fall data vectors directly set by the corresponding users or owners among the fall data vectors measured by the angular velocity sensor 13 and the triaxial acceleration sensor 14.

That is, the basic fall database 11 stores fall data vectors previously established before the user uses the fall detecting apparatus, while the user fall database 12 stores, in real time, fall data vectors measured when the user falls down.

Therefore, the fall detecting apparatus can determine the user's fall more correctly because its adaptation to the user becomes stronger as time passes by.

The angular velocity sensor 13 collects the variation of the angular velocity according to the user's fall. The angular velocity sensor 13 may include a gyro sensor.

It is known that the gravitational acceleration in the human body's movement ranges from 10 g to 20 g. However, an accelerometer with higher sensitivity is needed for detecting the user's fall, and the range of the gravitational acceleration in portions of the human body is various.

In this embodiment of the present invention, it is assumed that the triaxial acceleration sensor 14 has the sensitivity of −6 g to +6 g in the variation of the acceleration according to the human body's movement at a waist where the user wears the fall detecting apparatus for the purpose of good feeling in wearing and minimized inconvenience.

Further, the angular velocity sensor 13 and the triaxial acceleration sensor 14 measure data in unit of 100 ms.

The acceleration extractor 15 extracts the kinetic acceleration value (Ax, Ay, Az) by performing high-pass-filtering on the acceleration value measured by the triaxial acceleration sensor 14, and extracts the gravitational acceleration value (Tx, Ty, Tz) by performing low-pass-filtering on the acceleration value measured by the triaxial acceleration sensor 14.

A further description will be made below with reference to FIGS. 2A to 2C.

Figure 2A:
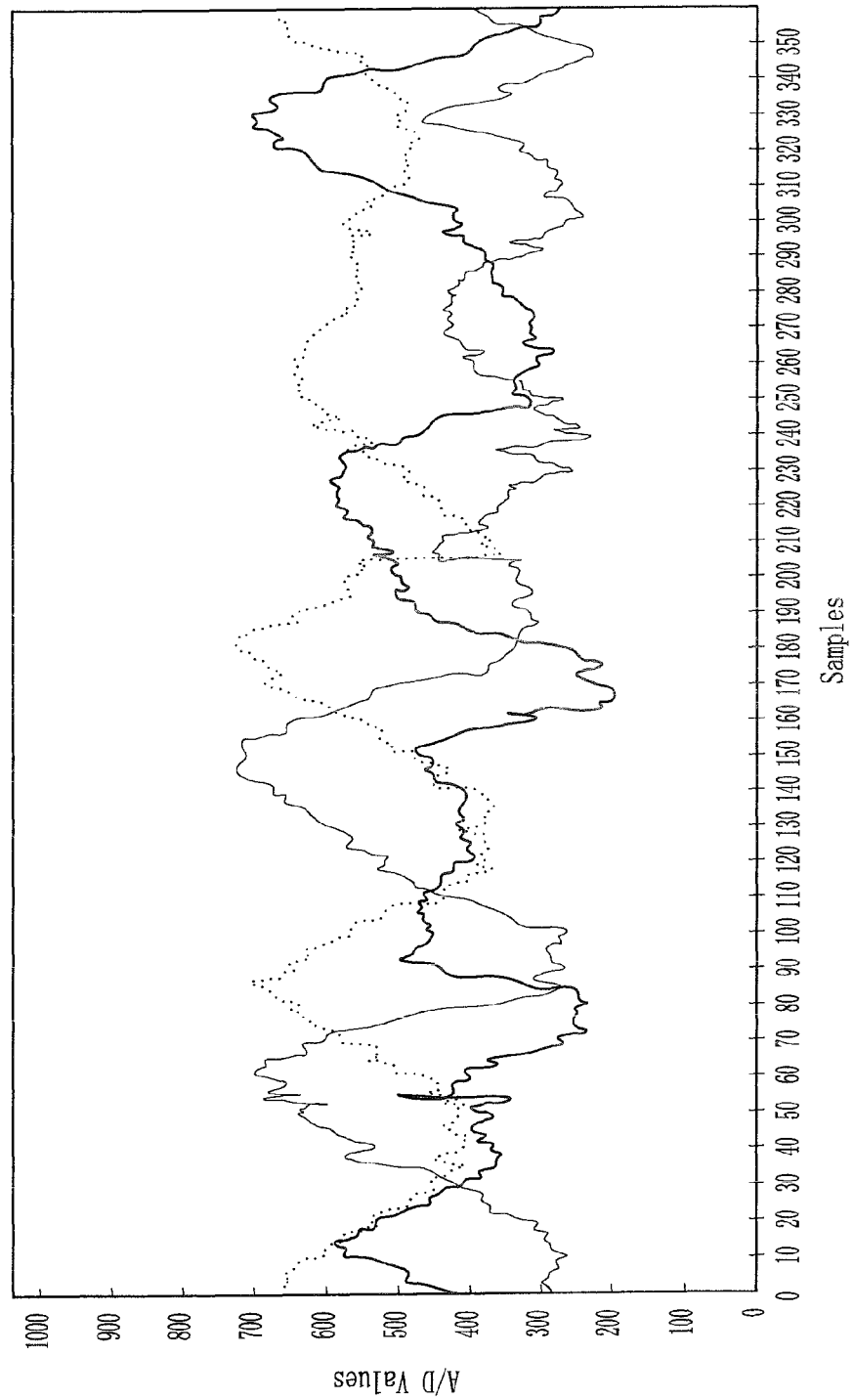
FIG. 2A is a graph showing an acceleration value measured by a triaxial acceleration sensor in accordance with an embodiment of the present invention.

As illustrated in FIG. 2A, the triaxial acceleration sensor 14 measures an acceleration signal, or a raw data, which includes both a kinetic acceleration component due to walking or action and a gravitational acceleration component due to a slope.

The kinetic acceleration component is located at a radio frequency component in a frequency domain, and the gravitational acceleration component is located at a low frequency component. Using these facts, the gravitational acceleration value is extracted through a low pass filtering as illustrated in FIG. 2B, and the kinetic acceleration value is extracted through a high pass filtering as illustrated in FIG. 2C.

Consequently, the variations of the acceleration and the slope in directions of x-axis, y-axis and z-axis can be known through the triaxial acceleration sensor 14.

The queue stores the fall data vectors in time unit of, for example, 1 second. If the fall data vector transmitted in unit of 100 ms is stored for 1 second, ten fall data vectors are always stored after 1 second. At this point, if a new fall data vector is added, the oldest fall data vector is deleted and a new fall data vector is stored.

The fall determining process of the fall determiner 16 will be described in more detail.

The fall determiner 16 determines the occurrence of the fall by calculating an approximation degree between the measured fall data vector (v) and the fall data vector (v1) stored in the basic fall database 11 or the fall data vector (v2) stored in the user database 12. The fall determiner 16 determines that the user falls down when the approximation degree expressed as the following Equation 1 is less than a threshold value.

$$Diff(v) = \alpha \sum_{i=1}^{n} \sqrt{w_i(v_i - v1_i)^2} + \beta \sum_{i=1}^{n} \sqrt{w_i(v_i - v2_i)^2} \quad \text{Eq. 1}$$

where v represents a currently measured fall data vector, n represents an order of the vector, and $v_i$ represents an i-th fall data of v.

For example, when v is Ax Ay Az Tx Ty Tz Jx Jy Jz, the fall data is Az for i=3.

The vector v1 represents the fall data vector that is most similar to v among the fall data vectors stored in the basic fall database 11, and the vector v2 represents the fall data vector that is most similar to v among the fall data vectors stored in the user fall database 12.

The vectors v1 and v2 are the fall data vectors making the following Equation 2 have a minimum value.

$$\sum_{i=1}^{n} \sqrt{w_i(v_i - v_{ki})^2}, \quad \text{Eq. 2}$$
$$k = 1, 2, \ldots, m$$

where $v_k$ represents an arbitrary fall data vector stored in the basic fall database 11 or the user fall database 12, $v_{ki}$ represents an i-th fall data vector among arbitrary fall data vectors, and w represents a weight vector in which data of the vector v influences the fall.

α represents a weight value allocated to the basic fall database 11, and β represents a weight value allocated to the user fall database 12. The weight values α and β are expressed as the following Equation 3. The weight values α and β are proportional to the sizes of the corresponding databases.

$$\alpha = \frac{\theta \log(N_1)}{\theta \log(N_1) + (1-\theta)\log(N_2)} \quad \text{Eq. 3}$$
$$\beta = \frac{(1-\theta)\log(N_2)}{\theta \log(N_1) + (1-\theta)\log(N_2)}$$

where $N_1$ represents the size of the basic fall database 11, and $N_2$ represents the size of the user fall database 12.

The reliability of the basic fall database 11 is set to θ and the reliability of the user fall database 12 is set to 1−θ. That is, the normalization is performed such that the sum of the two reliabilities becomes 1. The reliability θ is determined by experimental values of various users.

Figure 3:
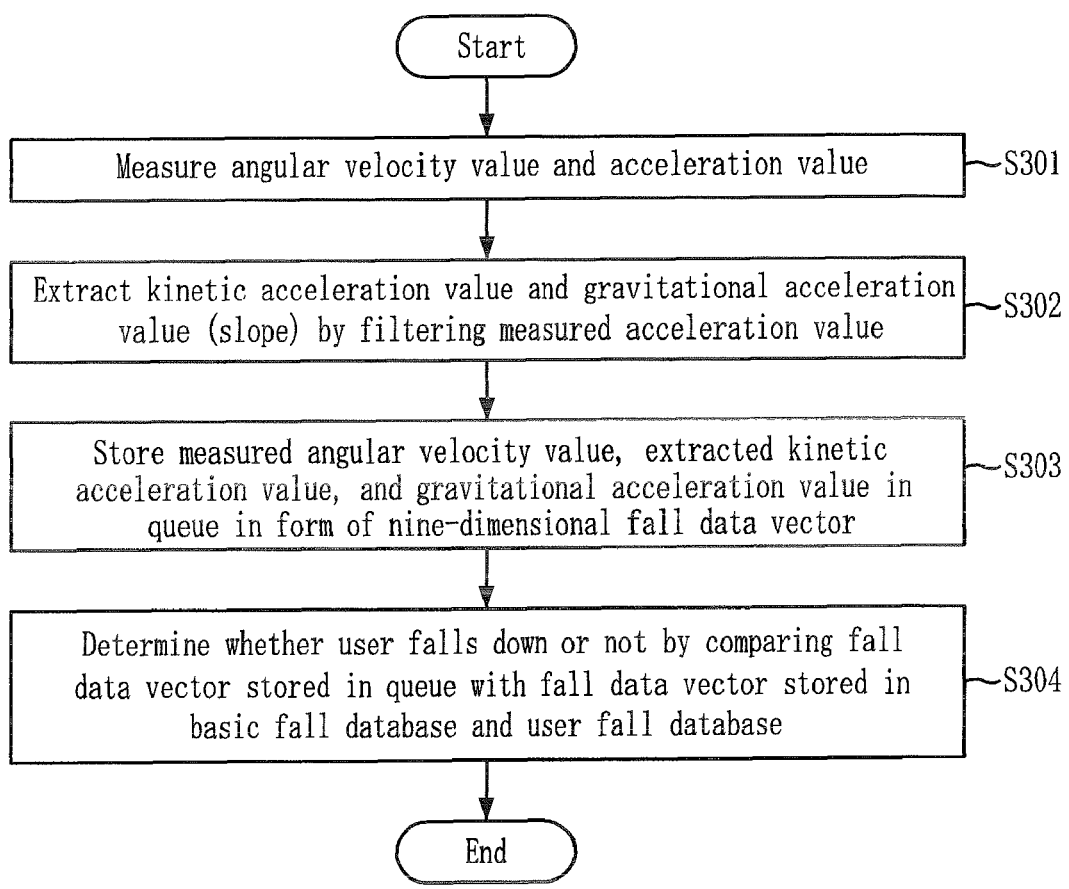
FIG. 3 is a flowchart describing a fall detecting method in accordance with an embodiment of the present invention.

FIG. 3 is a flowchart describing a fall detecting method in accordance with an embodiment of the present invention. Since the specified embodiment is identical to that described above, its operation will be briefly described below.

In step S301, an angular velocity value and an acceleration value are measured.

In step S302, a kinetic acceleration value and a gravitational acceleration or slope value are extracted by filtering the measured acceleration value.

In step S303, the measured angular velocity value, the extracted kinetic acceleration value and the extracted gravitational acceleration value are stored into a queue in form of nine-dimensional fall data vector.

In step S304, the occurrence of the fall is determined by comparing the fall data vector stored in the queue with the fall data vectors stored in the basic fall database 11 and the user fall database 12.

When it is determined in step S304 that the user falls down, the fall detecting method may further include the steps of acquiring the location information from the GPS satellite, and notifying the acquired location information and the fall notification information to the external emergency aid system. The fall notification information includes the user's private number.

Although it has been described in the above embodiment that the fall detecting apparatus can collect and determine the walking and behavior pattern information, these functions can be implemented by separate modules: a sensor module and a determination module.

That is, the sensor module includes the angular velocity sensor 13, the triaxial acceleration sensor 14, and the acceleration extractor 15, which periodically collect the kinetic acceleration value, the gravitational acceleration value, and the angular velocity value, respectively.

The sensor module may further include a communication module for transmitting the collected sensing data to the determination module. The communication module may use a Zigbee communication scheme.

The sensor module may further include a power switch for turning the power on/off, and a light emitting diode (LED) for indicating an on-state and a battery state.

Preferably, the sensor module is formed in ultra-small size so that the elderly persons can easily wear the fall detecting apparatus. Further, the triaxial acceleration sensor and the angular velocity sensor for collecting the walking and behavior patterns and the Zigbee chip for transmitting the collected sensing data to a portable terminal in a wireless communication can be integrated into a single module.

The determination module includes the basic fall database 11, the user fall database 12, and the fall determiner 16 and determines the occurrence of the fall from the sensing data collected by the sensor module.

The determination module includes a communication unit for receiving the sensing data from the sensor module. The communication unit may use a Zigbee communication scheme.

Figure 4:
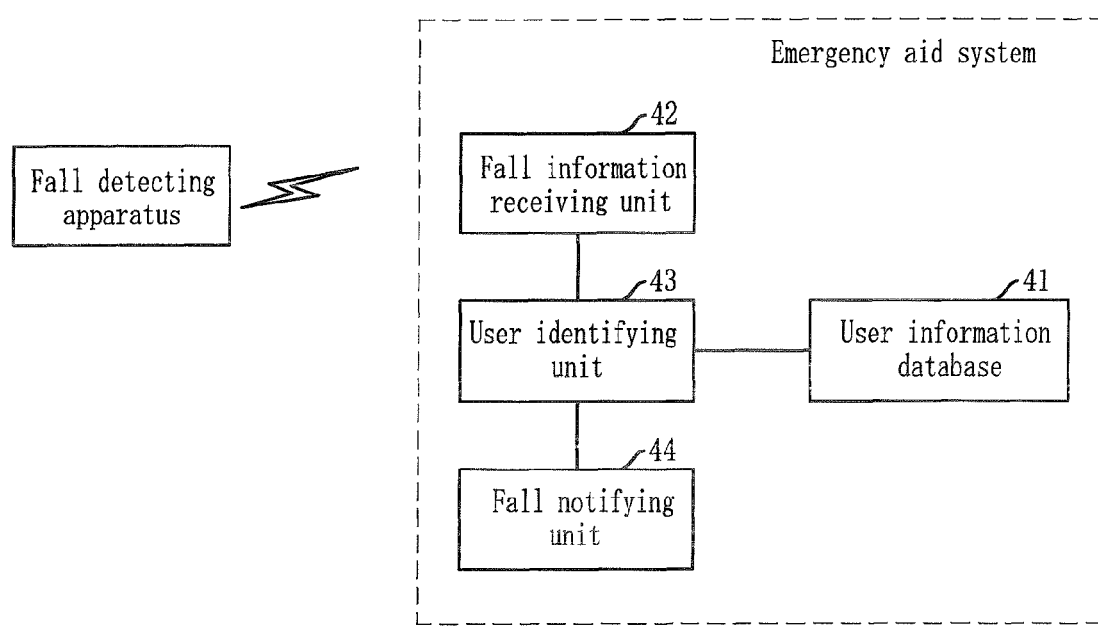
FIG. 4 is a block diagram of an emergency aid system using the fall detecting apparatus in accordance with an embodiment of the present invention.

FIG. 4 is a block diagram of an emergency aid system using the fall detecting apparatus in accordance with an embodiment of the present invention.

Referring to FIG. 4, the emergency aid system includes a user information database 41, a fall information receiving unit 42, and a user identifying unit 43, and a fall notifying unit 44. The user information database 41 stores personal information and health condition based on user's private number, and emergency contact number. The fall information receiving unit 42 receives the location information and the fall notification information from the fall detecting apparatus. The user identifying unit 43 confirms the user's identification by searching the user information database 41 on the basis of user's private number included in the fall notification information received by the fall information receiving unit 42. The fall notifying unit 44 notifies the user's fall to the emergency contact number of the user identified by the user identifying unit 43.

The fall notifying unit 44 may notify the user's fall via an SMS message, an MMS message, or a service operator.

The emergency contact number includes a family's phone number, a 119 emergency service call number, and a designated hospital's phone number.

FIG. 5 is a flowchart describing an emergency aid method using the fall detecting apparatus in accordance with an embodiment of the present invention. Since the specified embodiment is identical to that described above, its operation will be briefly described below.

In step S501, the location information and the fall notification information are received from the fall detecting apparatus.

In step S502, the user's identification is confirmed by searching the user information database on the basis of the user's private number included in the received fall notification information.

In step S503, when it is determined that the user falls down, the user's fall is notified to the emergency contact number.

As described above, unexpected accidents due to a fall can be quickly coped with by detecting, in real time, an accidental fall often occurring in a real life of elderly persons or mobility-impaired persons and notifying the accidental fall to the emergency aid system.

Further, the fall detecting apparatus for automatically detecting the accidental fall in real time uses the small-sized sensor module so that the elderly persons can easily wear it. Furthermore, since the portable terminal is used, the elderly persons can enjoy their safe life everyday, without regardless of place and time. Thus, the families can feel easy.

By being deployed in nursing homes, homes for the elderly persons, and other facilities, the apparatus and system of the present invention can quickly cope with accidental falls, and reduce the workload on nursing personnel and thus the burden of social welfare costs for seniors.

The present invention can be applied to the emergency aid service for accidental falls.

The methods in accordance with the embodiments of the present invention can be realized as programs and stored in a computer-readable recording medium that can execute the programs. Examples of the computer-readable recording medium include CD-ROM, RAM, ROM, floppy disks, hard disks, magneto-optical disks and the like.

While the present invention has been described with respect to the specific embodiments, it will be apparent to those skilled in the art that various changes and modifications may be made without departing from the spirit and scope of the invention as defined in the following claims.

What is claimed is:

1. A fall detecting apparatus, comprising:
   a storing unit configured to store fall data vectors;
   an angular velocity measuring unit configured to measure an angular velocity value;
   an acceleration measuring unit configured to measure an acceleration value;
   an acceleration extracting unit configured to extract a kinetic acceleration value and a gravitational acceleration value by filtering the acceleration value measured by the acceleration measuring unit; and
   a fall determining unit configured to convert the angular velocity value, which is measured by the angular velocity measuring unit, and the kinetic acceleration value and the gravitational acceleration value, which are extracted by the acceleration extracting unit, into a fall data vector, and determine a user's fall by comparing the converted fall data vector with the fall data vector stored in the storing unit.

2. The fall detecting apparatus of claim 1, further comprising:
   a location information acquiring unit configured to acquire location information; and
   a communication unit configured to notifying the location information, which is acquired by the location information acquiring unit, and fall notification information, which is generated by the fall determining unit, to an external emergency aid system.

3. The fall detecting apparatus of claim 1, wherein the storing unit includes:
   a basic fall database configured to store basic fall data vectors; and
   a user fall database configured to store user fall data vectors.

4. The fall detecting apparatus of claim 3, wherein the fall determining unit stores the angular velocity value, which is measured by the angular velocity measuring unit, and the kinetic acceleration value and the gravitational acceleration value, which are extracted by the acceleration extracting unit, into a queue in form of fall data vector, and determines the user's fall by comparing the fall data vector stored in the queue with the fall data vectors stored in the basic fall database and the user fall database.

5. The fall detecting apparatus of claim 4, wherein the fall determining unit determines the user's fall when an approximation degree between the fall data vector stored in the queue and the fall data vector stored in the basic fall database or the user database is less than a threshold value.

6. The fall detecting apparatus of claim 3, wherein the acceleration extracting unit extracts the kinetic acceleration value by performing high-pass-filtering on the acceleration value measured by the acceleration measuring unit, and extracts the gravitational acceleration value by performing low-pass-filtering on the acceleration value measured by the acceleration measuring unit.

7. A fall detecting method, comprising the steps of:
   measuring an angular velocity value and an acceleration value, by a measuring unit;
   extracting a kinetic acceleration value and a gravitational acceleration value by filtering the acceleration value, by an extracting unit;
   converting the measured angular velocity value, the measured kinetic acceleration value, and the measured gravitational acceleration value into a fall data vector, by a converting unit; and
   determining a user's fall by comparing the converted fall data vector with a preset fall data vector, by a determining unit.

8. The fall detecting method of claim 7, further comprising the steps of:
   acquiring location information when it is determined that a user falls down, by an acquiring unit; and
   notifying the acquired location information and the determined user's fall information to an external emergency aid system, by a communication unit.

9. The fall detecting method of claim 7, wherein the user' fall is determined when an approximation degree between the converted fall data vector and the fall data vector stored in a basic fall database or a user fall database is less than a threshold value.

10. The fall detecting method of claim 9, wherein the step of extracting the acceleration value includes the steps of:
    extracting the kinetic acceleration value by performing high-pass-filtering on the measured acceleration value; and
    extracting the gravitational acceleration value by performing low-pass-filtering on the measured acceleration value.

* * * * *